United States Patent
Lin

(10) Patent No.: US 7,393,453 B2
(45) Date of Patent: Jul. 1, 2008

(54) METHOD FOR ANALYSIS OF PERCHLORATE

(76) Inventor: Kham Lin, 121 Panorama Hills Circle NW, Calgary, Alberta (CA) T3K 4X5

( * ) Notice: Subject to any disclaimer, the term of this patent is extended or adjusted under 35 U.S.C. 154(b) by 365 days.

(21) Appl. No.: 11/366,974

(22) Filed: Mar. 3, 2006

(65) Prior Publication Data

US 2006/0144786 A1    Jul. 6, 2006

Related U.S. Application Data

(63) Continuation-in-part of application No. 11/036,936, filed on Jan. 18, 2005, now abandoned.

(60) Provisional application No. 60/581,710, filed on Jun. 23, 2004.

(51) Int. Cl.
*B01D 15/08* (2006.01)

(52) U.S. Cl. .................. 210/635; 210/656; 210/198.2; 210/502.1; 436/161

(58) Field of Classification Search .............. 210/635, 210/656, 683, 198.2, 502.1, 902; 436/161; 73/61.52
See application file for complete search history.

(56) References Cited

U.S. PATENT DOCUMENTS

| | | | | |
|---|---|---|---|---|
| 4,042,327 | A * | 8/1977 | Haney et al. | 436/161 |
| 4,820,644 | A * | 4/1989 | Schafer et al. | 436/518 |
| 5,310,885 | A * | 5/1994 | Maier et al. | 530/413 |
| 5,559,039 | A * | 9/1996 | Williams | 436/161 |
| 6,531,065 | B2 * | 3/2003 | Gurol et al. | 210/669 |
| 7,186,340 | B1 * | 3/2007 | Rittmann et al. | 210/604 |
| 2002/0084229 | A1 * | 7/2002 | Gurol et al. | 210/748 |
| 2005/0133458 | A1 * | 6/2005 | Gurol | 210/748 |
| 2006/0186049 | A1 * | 8/2006 | Boyes et al. | 210/656 |

* cited by examiner

*Primary Examiner*—Ernest G Therkorn

(57) ABSTRACT

A method for analyzing the content of perchlorate in a sample matrix comprising the steps of extracting the sample matrix and applying it to a reverse phase column, followed by elution with a mobile phase. The reverse phase column optionally has a protein coating deposited thereon.

12 Claims, 1 Drawing Sheet

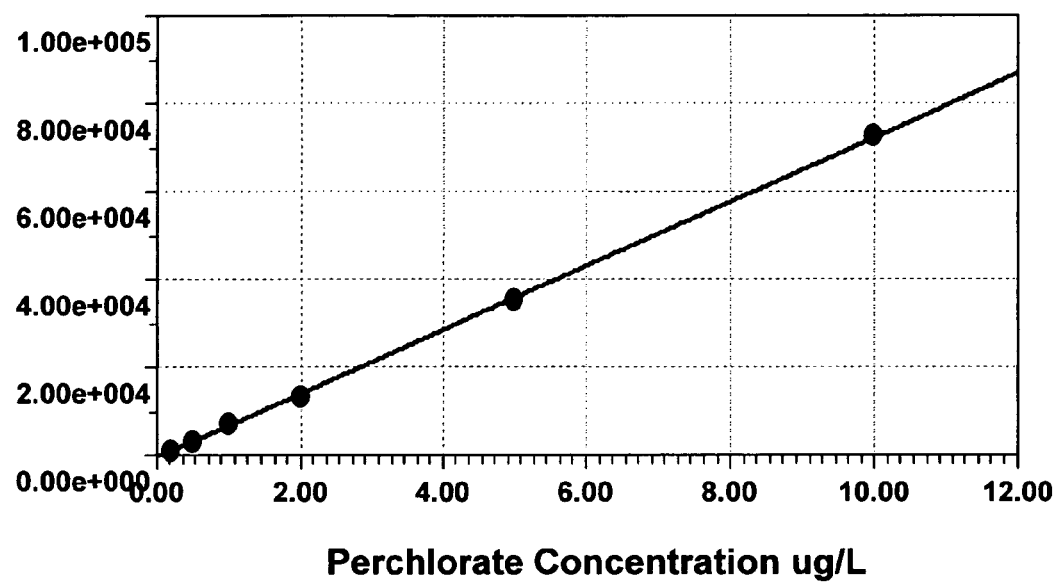

METHOD FOR ANALYSIS OF PERCHLORATE

CROSS REFERENCE TO RELATED APPLICATION

This application is a continuation in part of application Ser. No. 11/036,936, filed on Jan. 18, 2005 now abandoned, which claimed priority to provisional application No. 60/581,710, filed Jun. 23, 2004.

FIELD OF THE INVENTION

This invention relates to a method for the analysis of trace levels of perchlorate. More particularly, the method involves the use of liquid chromatography on a reverse phase to provide an enhanced sensitivity and resolution over conventional methods.

BACKGROUND

Perchlorate is an anion that exists in the environment as a part of other compounds, paired with cations such as in ammonium, potassium, or sodium perchlorates. Ammonium perchlorate, which comprises the bulk of manufactured perchlorate, is used as an oxygen-adding component in solid fuel propellant for rockets, missiles, and fireworks. Because of its limited shelf-life, inventories of ammonium perchlorate must be periodically replaced. Thus, large volumes of the compound have been disposed of since the 1950's.

Recent studies have shown that perchlorate can affect the thyroid gland, and, therefore, affect metabolism, growth, and development. Due to these studies, the Federal Environmental Protection Agency (EPA) has placed perchlorate on its Contaminant Candidate List for further study and potential regulatory action. Both California and Nevada have set action levels of eighteen parts per billion for perchlorate under their drinking water regulations. In a report published in January of 2002, the EPA have set a proposed action limit for perchlorate at 1.5 parts per billion. Because current regulatory actions regarding perchlorate have begun and future regulatory actions regarding perchlorate appear certain, regulatory agencies have focused upon testing methods for perchlorate.

Perchlorate is currently detected and quantified using ion chromatography. The two steps to this process are: (1) extraction and separation of perchlorate from all other species in a sample, and (2) measurement of the separated perchlorate against suitable standards. There are problems associated with obtaining low levels of perchlorate in certain types of samples using the standard ion chromatography configuration. Interferences caused by a large amount of anionics other than perchlorate within a sample can lead to false positives and/or reduced detection limits. The federal EPA method suggests that pretreating the sample through dilution can potentially assist with these problems, but the dilution may cause a reduction of the concentration of the target analyte to the point where it becomes undetectable. These problems are especially problematic in samples obtained from sources that contain extremely complex matrices of components, such as seawater. In practice, this current detection method is capable of relatively low detection levels of perchlorate in samples with low levels of ionic interferences. However, prior to the present invention, no known analysis method or device can meet the proposed action limit being considered by the EPA mentioned above.

The method of the present invention overcomes the limitations of the ion chromatography method by use of reverse phase liquid chromatography, coupled with a mass spectrometric detection method.

Liquid chromatography is a technique for separating the individual compounds that exist in a subject sample. In employing the technique, the subject sample is carried in a liquid, called a mobile phase. The mobile phase carrying the subject sample is caused to migrate through a media, called a stationary phase. Different compounds will have differing rates of migration through the media, which effects the separation of the components in the subject sample. Liquid chromatography is commonly performed with reusable columns or with disposable cartridges, both of which are usually cylindrical, in which the media bed is bounded axially by porous plates, or plates containing defined flow paths, through which the mobile phase will flow. (See U.S. Pat. No. 4,250,035 to McDonald et al. and U.S. Pat. No. 5,601,708 to Leavesley)

A significant element in the LC system is the column. A typical column usually consists of a piece of steel tubing which has been packed with a "packing" material. The "packing" consists of either particulate material "packed" inside the column, or a monolithic porous phase. It usually consists of silica-or polymer-based particles, which are often chemically bonded with a chemical functionality. When the sample is carried through the column (along with the mobile phase), the various components (solutes) in the sample migrate through the packing within the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components. A more detailed description of the separation process can be found, among other places, in Chapters 2 and 5 of Introduction to Modern Liquid Chromatography (2d ed. 1979) by L. R. Snyder and J. J. Kirkland, which chapters are incorporated by reference herein.

SUMMARY OF THE INVENTION

The present invention related to a method for analyzing perchlorate on a reverse phase HPLC column. In one embodiment of the invention the method comprises the steps of;

i. providing an extract of a sample, said extract containing the perchlorate to be quantified, ii. applying the extract to a stationary phase support, iii. eluting the extract with a mobile phase comprising an organic solvent, water and organic acid, and iv. detecting the eluted perchlorate.

In a further embodiment the support material is treated so as to cover the surface with a molecular layer that renders it suitable for reverse phase chromatography. The support material can be any inorganic or organic substance that provides sufficient mechanical strength to the packing and a sufficient degree of chemical functionality for the application. Non limiting examples of support materials include, without limitation, silica, alumina, zirconia, polystyrene, polyacrylamide, and styrene—divinyl benzene copolymers. In a particular embodiment of the invention, the molecular layer is an alkyl moiety, preferably octadecyl.

In a further embodiment the stationary reverse phase support comprises an alkylated base material, said base material being selected from the group consisting of silica, alumina, zirconia, polystyrene, polyacrylamide, and styrene-divinyl copolymers.

In a still further embodiment of the invention, the material is further treated by coating with a protein layer that comprises protein, polypeptide, or other proteinaceous material. The protein coating may be covalently bonded to the material, or adsorbed thereon.

In a still further embodiment of the method of the invention the organic solvent is selected from the group consisting of methanol, ethanol, acetonitrile, ethyl acetate, and 2-propanol. In a still further embodiment of the method of the inventions, the mobile phase has a composition of between 5% and 95% by volume of organic solvent, 5% and 95% by volume of water and 0.05% and 5% by volume of organic acid.

The surface of said alkylated base material can be alkylated with hydrocarbon chains containing from 4-18 carbon atoms.

The perchlorate may be detected by mass spectrometry, preferably the perchlorate is detected at a mass of 83 and 85.

In a still further embodiment of the method of the invention the method comprises the step of adding an internal standard to the extract. Preferably the internal standard comprises perchlorate in which O16 is partially replaced by heavy Oxygen (O18). Said internal standard may be detected at a mass of 89 or 91 or both 89 and 91 together. In a further embodiment of the method of the invention, the isotopic mass ratios of chlorine 35 to chlorine 37 in the perchlorate standard comprising O18 are used for confirmation.

DESCRIPTION OF THE FIGURES

FIG. 1 shows a calibration curve for the method of the invention.

DETAILED DESCRIPTION OF THE INVENTION

Definitions

"Extract" as used herein means either an extract of an solid sample obtained by solvent extraction, or a liquid sample that may or may not be subjected to a solvent extraction step.

"Protein coating" in the context of the stationary phase material refers to the fact that a coating of protein, polypeptide or other proteinaceous material has been attached to the surface of the material either by covalent, physical, or other type of chemical bonding.

Processes for immobilization of proteins on solid phases are known in the art, for examples, U.S. Pat. Nos. 5,310,885 and 5,559,039, both incorporated herein by reference in their entirety. Although examples are given here to guide one skilled in the art in preparation of a suitable column for the process of the invention, the invention is not to be construed as being limited to columns prepared by these methods, and any column for liquid chromatography that has been subjected to coating by protein, peptide, polypeptide or other proteinaceous material is suitable for the process of the invention.

The fixing of a protein on a solid phase can take place by chemical or physical means. Proteins can be adsorbed from a solution onto a solid phase. Methods for the production of covalent bonds between a solid carrier material and proteins to be bound thereon are known. For example, European Patent Specification No. 0,274,911, herein incorporated by reference, describes the use of chemically reactive synthetic resin membranes which are able to covalently bind proteins directly.

Processes are also known in which reactive groups of the solid phase are coupled with a bifunctional linker, where the remaining free functional group of the linker is covalently bound to the protein to be fixed. U.S. Pat. No. 4,820,644, herein incorporated by reference, describes, for example, processes for fixing an immune-reactive material on a porous carrier material. In order to avoid problems of adhesion on the carrier material, the fixing is achieved by allowing an immune reaction to take place between the two partners of an immune reaction, i.e. between an antibody and an antigen or hapten. An immune complex mesh is formed which contains the protein to be bound (antibody or antigen) and this mesh binds on to the solid phase.

British Patent Specification No. 1,505,400, herein incorporated by reference, suggests cross-linking an immunologically active protein and then absorbing it on polystyrene latex particles, the adsorption being carried out in a latex emulsion. After the binding of a part of the protein on the latex particles, these are centrifuged off and washed several times. The protein-carrying polystyrene particles are stored as a suspension in buffered aqueous solutions and used for separation reactions.

European Patent Specification No. 0,122,209, herein incorporated by reference, describes a process for binding biological macromolecules on to solid phases which comprises polymerizing the macromolecules to be fixed, incubating for several hours together with hydrophobic carrier materials, for example polystyrene, and, after binding of a part of the polymerized macromolecules on to the carrier material, washing this several times before use or storage.

European Patent Specification No. 0,269,092, herein incorporated by reference, discloses a process for improving the adhesion in comparison with the two above-mentioned processes. For this process, the protein to be fixed is fixed covalently to a hydrophobic carrier protein and the complex obtained is adsorbed on a hydrophobic solid phase. By utilization of the hydrophobic exchange action between the solid phase and the carrier protein, an especially advantageous fixing is thereby achieved.

An approach that eliminates most constraints on the internal partitioning phase is to coat the packing with sufficient protein to prevent further protein adsorption. When large amounts of serum albumin or plasma are loaded onto an ODS-silica column, the column adsorbs no further protein and is said to be saturated. The silica is selected to have a pore size that excludes the protein from the pores so that the internal reverse phase remains unfouled and separatively active towards small lipophilic solutes such as drugs in plasma.

Most of the coating can be permanently attached by passing 100% methanol through the column to denature and physically crosslink the coating. However, some saturation is lost after applying this crosslinking method, so that the entire treatment must be performed several times. After several cycles of saturation followed by denaturation, a permanently saturated column results. Such columns have been used to directly inject plasma and serum samples for LC analysis of drugs. See, e.g., H. Yoshida et al, "Some Characteristics of a Protein-Coated ODS Column . . . ", Chromatographia, Vol. 19, 1985, pp. 466-472.

A further approach to imparting a crosslinked protein coating onto packing materials employs simultaneous contact of glutaraldehyde with a concentrated solution of protein in an unbonded silica slurry in water. The object of this approach is to maximize the amount of immobilized protein short of creating an impermeable composite through which liquid could not readily flow. In this approach, the weak adsorption properties of the immobilized protein in the packing material are useful. See, e.g., M. Tsuboi et al, "Chromatography Carrier", Japanese Patent Application No. 198,334/85, Sep. 7, 1985. A similar method uses a two-stage glutaraldehyde crosslinking procedure in which the crosslinking was interrupted after a period of time by washing away serum albumin that had not yet deposited on the silica. Subsequently, more glutaraldehyde was added to ensure that the remaining albumin was tightly crosslinked and permanently attached to the silica. The two stage process ensured that large clumps of support particles were not glued together. Such clumps disrupt flow through the column and degrade efficiency. See, e.g., R. A. Thompson et al," . . . Sorbents Obtained by Entrapment of Crosslinked Bovine Serum Albumin in Silica", Journal Chromatography, Vol. 465 (1989) pp. 263-270.

Yet another approach to forming a protein coating is to use glutaraldehyde as a coupling agent in a first step by bonding it to an aminopropyl-silica, leaving an immobilized aldehyde residue to which in a second step protein can be bonded through the amino side chain of lysine amino acid residues. Often sodium cyanoborohydride or pyridine borane is used to stabilize the bond to the packing by reducing the intermediate imine to the secondary amine. It is common in a final step to block residual immobilized aldehyde by addition of an excess of some hydrophilic primary amine such as tris (hydroxymethyl) aminomethane, glycine, or ethanolamine to avoid non-specific bonding by aldehyde during affinity chromatography. See, e.g., F. R. Bernath et al, "Methods of Enzyme Immobilization", in Manual of Industrial Microbiology and Biotechnology, ed. A. L. Deman & N. A. Solomon, publ. Amer. Soc. Microbiology, Wash. D.C. (1986) pp. 244-5. This approach immobilizes protein by forming covalent bonds between it and the support.

By "packing material" is meant the stationary phase support used in the process. The column is packed with a material that comprises a support material that has been treated so as to cover the surface with a molecular layer that renders it suitable for reverse phase chromatography. The support material can be any inorganic or organic substance that provides sufficient mechanical strength to the packing and a sufficient degree of chemical functionality for the application. Examples of support materials include, without limitation, silica, alumina, zirconia, polystyrene, polyacrylamide, and styrene—divinyl benzene copolymers. In a particular embodiment of the invention, the molecular layer is an alkyl moiety, preferably octadecyl.

By "mobile phase" is meant the liquid carrier that is pumped through the column and is used to move the analyte through the column as the analyte partitions between it and the stationary phase support. In the present invention the stationary phase comprises a mixture of an organic solvent, water and an organic acid. Examples of suitable solvents include, but are not limited to, methanol, ethanol, acetonitrile, ethyl acetate, and 2-propanol. Examples of organic acids include but are not limited to acetic, formic, and proprionic acids.

The composition of the mobile phase can vary between 5% and 95% of organic solvent, 5% and 95% of water, and 0.05% and 5% or organic acid. The composition need not be constant during a run, and a solvent composition gradient may be used.

Description of the Embodiments

The present invention related to a method for analyzing perchlorate on a reverse phase HPLC column.

In an embodiment of the invention, an internal standard is added to a sample matrix. Solid sample matrices are extracted using a suitable solvent or solvent mixture and the extract is injected onto a stationary phase support, optionally in a mobile phase as described above. A suitable solvent for extraction would be any water or organic solvent based liquid, and one skilled in the art would be able without undue experimentation to establish a suitable composition. Non solid sample (liquid sample) may be injected directly onto a stationary phase support, optionally in a mobile phase as described above. The extract is then eluted with the mobile phase, and the perchlorate is detected by a suitable detector when it comes off the stationary phase support in the mobile phase. An example of a suitable detector for the invention is a mass spectrometric detector, for example the Agilent 1100 series HPLC/MSD (Agilent Technologies, Palo Alto, Calif.).

In a preferred embodiment of the invention, the internal standard is a perchlorate sample in which the O16 of the perchlorate has been partially or completely substituted with heavy oxygen (O18).

In a further embodiment of the invention, the stationary phase support comprises a material that has been treated so as to cover the surface with a molecular layer that renders it suitable for reverse phase chromatography. In a particular embodiment of the invention, the molecular layer is an alkyl moiety, preferably octadecyl. In a still further embodiment of the invention, the material is further treated by exposure to a proteinaceous material that provides a protein coating on the stationary phase support.

EXAMPLES

The invention can be further understood with reference to the following example.

An Agilent 1100 LC/MSD system (Agilent Technologies, Palo Alto, Calif.) was utilized for this method. This method uses simple determinative techniques available to normal LC/MS technologies and does not require any instrumentation additions or systematic pretreatment of samples. The analysis is accomplished in under 15 minutes and can process up to 30 samples in an eight hour sequence with all appropriate quality control and additional perchlorate identification by mass spectrometry.

The Agilent 1100 LC/MSD system (with part numbers) consisted of a binary pump G1312A, a micro-degasse G1379A, autosampler G1313A, column compartment G1316A, 1100 LC/MSD G2708DA, and Agilent LC/MSD Chemstation software G2710AA.

Instrument conditions were as follows.

| | |
|---|---|
| Pump Flow | 0.5 to 0.6 ml/min |
| Mobile Phase | 53% Eluent A, 47% Eluent B |
| Sample Volume | 1.0-100.0 ul |
| Column Temp | 35° C. |
| LC/MSD setting | SIM Mode (masses 83, 85, 89 and 91), Fragmentor Voltage 200-240, Dry Gas 12 L/min, and Cap Voltage 3000. |

The column was a Zorbax XDB C-8 (Agilent Technologies, Palo Alto, Calif.) that had been treated by injection with a methanol extract of pork tissue. Injections were carried out with a mixture of acetonitrile and water (50% by volume of each) plus 0.1% by volume of acetic acid.

Eluents were prepared with ASTM Type II water and acetonitrile (CAN). Eluent A consisted of 95% ACN and 5% water, with a small aliquot of acetic acid (approximately 0.1%). Eluent B consisted of 95% water, and 5% ACN, with a small aliquot of acetic acid (approximately 0.1%). The solutions from the two bottles will be mixed at the instrument pump at 53% eluent A and 47% eluent B.

Standard concentrations used to calibrate were 0.2, 0.5, 1.0, 2.0, 5.0, and 10.0 µg/L. The standards were prepared in a 50% ACN, and 0.1% acetic acid solution. The Internal Standard of Oxygen-18 labeled perchlorate (O18LP) was at 5.0 μg/L, and added to each standard and sample.

A minimum of six calibration standards was used for internal standard calibration. The standard curve for perchlorate was established by plotting the area for each standard/internal standard ratio against the concentration. The calibration was verified immediately after calibration by the analysis of an Initial Calibration Verification (ICV) Standard. The ICV was prepared from a separate source of perchlorate at 1.0 ug/L.

Continuing Calibration Verification (CCV) standards were used for each analysis batch prior to conducting any analysis, every tenth sample, and at the end of the analysis sequence.

Sample Preparation

Water samples were prepared by adding an aliquot of sample to a 15-mL disposable centrifuge tube. An appropriate aliquot of O18LP and glacial acetic acid was added to each sample. Each sample was filtered through a 0.45-μm filter into an autosampler vial for analysis.

Soil samples were prepared by adding an aliquot of sample and 10 mL of ASTM Type II water to a 15-mL centrifuge tube. An appropriate aliquot of O18LP and glacial acetic acid was added to each sample. The mixture was vortexed, then sonicated for at least 10 minutes. If necessary, the sample was centrifuged. The extract was then filtered through a 0.45-μm filter into an autosampler vial for analysis.

Biota (Plant) samples were prepared by using at least 10 grams of sample. The sample was ground through a hand-operated stainless steel grinder. 30 mL of ASTM Type II water is added to an aliquot of biota sample in a 50-mL centrifuge tube. An appropriate aliquot of O18LP and glacial acetic acid is added to each sample. The mixture was vortexed and left overnight, which allows for complete saturation of the sample. Prior to analysis, the sample is vortexed again, then centrifuged at 5000 rpm for 30 minutes. A portion of the supernatant was then drawn through an activated C18 column, which removes a large portion of organic contaminants. Supernatant was then filtered through a 0.45-μm filter into an autosampler vial for analysis. The five matrices evaluated by this LC/MS method are presented in Table 1.

TABLE 1

Matrix Description and Preparation

| | |
|---|---|
| Drinking Water (DW) | Laboratory Distilled Water Conductivity = 1 uS |
| Soil | Soil extracted with water |
| Biota | Grass Sample were homogenized, extracted with water and C-18 column cleanup |
| Synthetic Ground Water (SGW) | Laboratory Distilled Water with 1000 mg/l of chloride, sulfate, and carbonate. Conductivity = 7700 uS |
| Great Salt Lake (GSL) Water | Water taken from the Great Salt Lake and diluted 10x Conductivity = 21000 uS |

Method Detection Limits (MDL) studies following the USEPA procedure ("Determination of Perchlorate in Drinking Water using Ion Chromatography" USEPA Method 314.0, Rev 1, November 1999) were analyzed to determine sensitivity of this LC/MS method. Practical Quantitation Limits (PQL) in aqueous, soil and biota samples were based of the DoD Quality System Manual (Department of Defense Quality Systems Manual for Environmental Laboratories, Final version 2, June 2002) guidance.

Mass spectrometry was used to monitor perchlorate at mass 83, which was achieved by the partial fragmentation of perchlorate to remove an oxygen atom. Using mass 83 eliminates known interference caused by sulfate at mass 99. Confirmation of perchlorate was obtained not only by retention time and mass but also by using the naturally occurring isotopic ratio of chlorine 35 to 37 of 3.065 (The Condensed Chemical Dictionary, $10^{th}$ edition, Gessinger G. Hawley, 1981) to monitor the ratio of mass 83 and 85 from perchlorate. O18LB was used as an internal standard and added to each standard and sample. This internal standard was used for retention time confirmation, monitoring instrument performance, and internal standard calibration.

Precision and Bias validation studies were performed using the guidance presented in the NELAC 2003 Standard (EPA 600/R-04/003) Chapter 5, appendix C3. Briefly, five matrices including drinking water, soil, biota, simulated ground water, and saline water were spiked with perchlorate and analyzed. Three different concentrations in each matrix were analyzed on three consecutive days. Additionally, all samples submitted for analysis having difficult matrices and/or positive detections by method USEPA 314.0 were confirmed by this new method. A proficiency-testing sample was also analyzed to assess bias of this method.

A known amount of O18LB was added to each sample and standard and monitored at mass 89 as internal standard. The use of internal standard calibration adds stability to the calibration and eliminates the need for monitoring transition of perchlorate from mass 99 to 83.

Results

The calibration curve used for this study is presented in FIG. 1. Calibration acceptance criterion for the initial calibration curve is a correlation coefficient of 0.995 or higher. ICV and CCV calibration verifications are presented in Table 10 and control limits were set at ±15% from the true value.

Sensitivity

The minimum detection limit (MDL) for five matrices was calculated using the procedures specified by the USEPA (United States Code of Federal Register, Volume 40 Part 36, Appendix B). Seven aliquots of a fortified spike or indigenous level were analyzed. The MDL is calculated by multiplying the standard deviation of results by 3.143 (t statistic). The drinking water (DW), simulated ground water (SGW) and soil samples were spiked with perchlorate while indigenous levels of perchlorate in biota and Greater Salt Lake water (GSL) were used to calculate MDLs. The MDLs were additionally verified by analysis of a MDL verification sample for each matrix. This procedure is described in the DoD Quality System Manual (Department of Defense Quality Systems Manual for Environmental Laboratories, Final version 2, June 2002).

The PQL was set no less than the lowest calibration standard. Values below the PQL are reported with appropriate qualifiers. Additionally, the PQL was set at 3 to 5 times the MDL value. MDL and PQL data are presented in Table 2 and MDL Verification Results in Table 3.

TABLE 2

MDL and PQL Determinations

| Matrix | n | Spiked Conc. μg/L | Mean Conc μg/L | Standard Deviation μg/L | % RSD | Ratio | MDL μg/L | PQL μg/L |
|---|---|---|---|---|---|---|---|---|
| Drinking Water | 7 | 0.200 | 0.200 | 0.0108 | 5.40% | 5.89 | 0.0339 | 0.20 |
| Soil | 7 | 2.00 | 2.26 | 0.258 | 11.4% | 2.47 | 0.811 | 2.0 |
| Biota* | 7 | 4.49 μg/Kg | 4.49 | 0.609 | 13.6% | 2.34 | 1.92 | 6.0 |
| SGW | 7 | 0.200 | 0.209 | 0.0257 | 12.3% | 2.48 | 0.0807 | 0.20 |
| GSL* | 7 | 0.219 | 0.219 | 0.0196 | 8.96% | 3.55 | 0.0617 | 0.20 |

*Indigenous levels in these matrices were used to calculate MDLs
SGW = Simulated Ground Water 1000 mg/L of Chloride, Sulfate, Carbonate (Conductivity = 7700 uS)
GSL = Great Salt Lake Water diluted 10X (Conductivity = 21,000 uS)

TABLE 3

MDL Verification Results

| Matrix | MDL Verification Concentration μg/L | MDL Verification Result μg/L |
|---|---|---|
| Drinking Water | 0.10 | 0.11 |
| Soil | 1.0 | 1.0 |
| Biota | 2.5 | 1.6 |
| SGW | 0.10 | 0.11 |
| GSL | 0.11 | 0.12 |

SGW = Simulated Ground Water 1000 mg/L of Chloride, Sulfate, Carbonate (Conductivity = 7700 μS)
GSL = Great Salt Lake Water diluted 10X (Conductivity = 21,000 μS)

Selectivity

Mass spectrometry was used to monitor perchlorate at masses 83 and 85. O 18LP is monitored at mass 89.

The ratio of 83/85 masses was monitored during this study for all matrices analyzed by this method. Statistical limits are shown for all concentrations in Table 4. Differences in measurement error discussed in "Experimental Statistics" (Handbook 91, United States Department of Commerce, National Bureau of Standards, Aug. 1, 1963) may have an impact on the low and medium concentration samples shown in Table 4. The results of this scatter plot and table shows a lower 83/85 mean ratio at low concentrations of perchlorate. Based on error of measurement associated with low levels and the importance of confirming perchlorate the 83/185 isotopic ratio statistical process control limits are set using ±2 standard deviations at 2.2 to 3.3 which is calculated as follows.

$$\text{MeanRatio}_{83/85} \pm (2 \times \text{Stdev}_{83/85})$$

TABLE 4

Perchlorate 83/85 Isotopic Ratio and Control Limits

Mean 83/85 Ratio by Concentration

| Low Conc | Average | 2.59 | Std Dev | 0.28 |
|---|---|---|---|---|
|  | LCL[1] | 1.74 | UCL[1] | 3.44 |
| Med Conc | Average | 2.73 | Std Dev | 0.32 |
|  | LCL[1] | 1.78 | UCL[1] | 3.68 |
| High Conc | Average | 2.89 | Std Dev | 0.20 |
|  | LCL[1] | 2.27 | UCL[1] | 3.50 |

TABLE 4-continued

Perchlorate 83/85 Isotopic Ratio and Control Limits

Total 83/85 Ratio

| Average | Std Dev | n | LCL[2] | UCL[2] |
|---|---|---|---|---|
| 2.75 | 0.29 | 121 | 2.16 | 3.34 |

[1]±3 SD,
[2]±2 SD

Precision and Bias

Validation studies based on NELAC Chapter 5 (2003 NELAC Standard, Chapter 5, Appendix C. 3, EPA 600/R-04/003) were generated for five matrices by analyzing samples over three consecutive days at varying concentration levels. The study designed analyzed nine replicates for each matrix on a daily basis. The three concentrations are at or near the limit of quantitation, at the upper-range of the calibration (upper 20%) and at a mid-range concentration.

Precision

To compare the variability of performance (precision) the F-Test was performed on each matrix. Matrices were evaluated based on concentration levels, and combined daily results. Data for this section is presented in Data Table I. The equations used in this section are discussed in "Experimental Statistics" (supra) and "Statistics for Analytical Chemistry" (statistics for Analytical Chemistry, J. C. Miller and J. N. Miller, 1984).

Table 5 summarizes precision for this method with respect to concentrations in same matrix.

The significance of $\square=0.01$ and Degrees of Freedom (DF=8) were used to determine critical values used to assess variability of performance. When using this test to compare the precision at different concentration levels the user must be concerned with the fact that errors of measurement (Experimental Statistics Handbook-supra) may have more affect on one of the concentrations.

Critical Values of $F_{0.1\text{-}\square}(8,8)$ and $1/F_{0.1}\text{-}\square(8,8)$ are 6.03 and 0.17, respectively.

The null hypothesis is stated as follows. If F>0.17 and F<6.03 then the variability of performance for this method with respect to concentrations in the same matrix is not different.

$$F = \frac{(RSD_{ConcX})^2}{(RSD_{ConcY})^2}$$

TABLE 5

Variability of Performance with Respect to Concentrations in the Same Matrix

| Matrix | Low Conc. vs. Med Conc. | Low Conc. vs. High Conc. | Med Conc. vs. High Conc. |
|---|---|---|---|
| Drinking Water | 2.86 | 8.05 | 2.81 |
| Soil | 1.18 | 3.52 | 2.98 |
| Biota | 0.38 | 1.88 | 4.98 |
| SGW | 2.70 | 9.79 | 3.62 |
| GSL | 0.71 | 2.15 | 3.03 |

Table 6 summarizes precision for this method with respect to daily analysis for all concentrations same matrix. The significance of □=0.01 and Degrees of Freedom (DF=8) was used to determine critical values used to assess variability of performance. Critical Values are the same as used for Table 4.

The null hypothesis is stated as follows. If F>0.17 and F<6.03 then the variability of performance for this method with respect to daily analysis for all concentrations in the same matrix is not different $$F = \frac{(RSD_{Day\#})^2}{(RSD_{Day\#})^2}$$

TABLE 6

Variability of Performance with Respect to Daily Analysis for all Concentrations in the Same Matrix

| Matrix | Day 1 vs. Day 2 | Day 1 vs. Day 3 | Day 2 vs. Day 3 |
|---|---|---|---|
| Drinking Water | 1.89 | 1.89 | 1.00 |
| Soil | 1.16 | 2.04 | 1.75 |
| Biota | 0.41 | 0.65 | 1.60 |
| SGW | 0.60 | 0.92 | 1.53 |
| GSL | 1.69 | 0.67 | 0.40 |

Table 7 summarizes precision for this method with respect to matrix for all concentrations on all days. The significance of □=0.01 and Degrees of Freedom (DF=26) were used to determine critical values used to assess variability of performance. Critical Values of $F_{0.1-\square}(26,26)$ and $1/F_{0.1-\square}(26,26)$ are 2.50 and 0.40, respectively.

The null hypothesis is stated as follows. If F>0.40 and F<2.55 then the variability of performance for this method with respect to matrix for all concentrations on all days is not different $$F = \frac{(RSD_{MatrixX})^2}{(RSD_{MatrixY})^2}$$

TABLE 7

Variability of Performance with Respect to Matrix for all Concentrations on all Days

| Matrix | Soil | Biota | SGW | GSL |
|---|---|---|---|---|
| Drinking Water | 1.46 | 0.95 | 0.51 | 0.69 |

Bias

Analysis of the data to determine if the method was biased with respect to aqueous matices was accomplished by multiple techniques.

A proficiency-testing sample analyzed by LC/MS and compared to analysis by method UPEPA 314.0 is presented in Table 8.

TABLE 8

Proficiency Testing Results

| PT Study | Result 314.0 | Result LC/MS | True Value |
|---|---|---|---|
| WS04-1 | 47.3 ug/L | 51.2 ug/L | 52.7 ug/L |

To compare the variability of the means of each aqueous matrix the Paired t-Test was used. The equations used in this section are discussed in "Experimental Statistics" and "Statistics for Analytical Chemistry". The differences between each pair of results on the aqueous matrices were calculated and the mean difference and mean standard deviation were computed. Data for this section is presented in Data Table II. For the Paired t-test the level of significance was p=0.99. The critical value of $t_{0.99}$ is 2.479. Table 9 summarizes the results of the Paired t-Test.

The null hypothesis is stated as follows. If |t|<2.479 the variability of means of each aqueous matrix with respect to this method are not significantly different.

$$t = MeanDifference_{MatixX-MatrixY} \times \frac{\sqrt{n}}{StdevDifference_{MatrixX-MatrixY}}$$

TABLE 9

Results of Paired t-Statistic for Aqueous Matrices

| Matrix: | DW vs. SGW | DW vs. GSL | SGW vs. GSL |
|---|---|---|---|
| |t| | 1.74 | 0.51 | 2.07 |

LC/MS confirmation of positive result for samples analyzed by method USEPA 314.0 was performed. Table 10 presents data on samples analyzed by both methods.

TABLE 10

LC/MS Confirmation of Perchlorate

| Sample Matrix | Result by USEPA 314.0 | Result by LC/MS | Confirmation Achieved |
|---|---|---|---|
| Water 04C00326 | 0.76 ug/L | 0.87 ug/L | Yes |
| Water 04C00327 | 0.87 ug/L | 1.1 ug/L | Yes |
| Water 04C00328 | 1.8 ug/L | 1.8 ug/L | Yes |
| Water 04C00329 | 1.6 ug/L | 1.8 ug/L | Yes |
| Water 04C00330 | 1.6 ug/L | 1.4 ug/L | Yes |
| Water 04C00331 | 1.2 ug/L | 1.5 ug/L | Yes |
| Water 04C00426 | ND | ND | Yes |
| Water 04E02488 | 0.36 | 0.40 | Yes |
| Water 04E01966 | 0.40 | 0.41 | Yes |

Robustness

A single calibration curve was used for this entire study. Results of CCV analysis during the validation study are presented in Table 11 and are used to assess the stability of the instrument calibration. Use of O18LP as an internal standard has reduced calibration runs and eliminates worrisome variation in the mass spectrometer due to matrix interferences. The internal standard area counts are monitored and must be within ± 30% of the daily calibration verification response. By using O18LP the retention time of naturally occurring perchlorate is the equivalent and fluctuations due to temperature and pressure are negated.

TABLE 11

Calibration Verification Results (Initial Calibration Mar. 18, 2004)

| Date/Time | Result | Nominal Value | % Difference |
|---|---|---|---|
| 4/2/04 4:29 PM | 10.45 | 10.0 | 4.5% |
| 4/2/04 7:16 PM | 1.005 | 1.00 | 0.5% |
| 4/2/04 9:48 PM | 9.25 | 10.0 | 7.6% |
| 4/3/04 5:24 AM | 0.998 | 1.00 | 0.2% |
| 4/3/04 11:52 AM | 10.45 | 10.0 | 4.5% |
| 4/3/04 2:40 PM | 0.949 | 1.00 | 5.1% |
| 4/3/04 5:12 PM | 10.51 | 10.0 | 5.1% |
| 4/3/04 7:44 PM | 0.989 | 1.00 | 1.1% |
| 4/3/04 10:16 PM | 10.66 | 10.0 | 6.6% |
| 4/4/04 9:52 AM | 11.008 | 10.0 | 10.1% |
| 4/4/04 12:39 PM | 1.027 | 1.0 | 2.7% |
| 4/4/04 3:11 PM | 10.14 | 10.0 | 1.4% |
| 4/4/04 5:43 PM | 0.983 | 1.0 | 1.7% |
| 4/4/04 8:15 PM | 10.52 | 10.0 | 5.2% |
| 4/4/04 10:47 PM | 1.015 | 1.00 | 1.5% |

The results described above and particular shown in tables 1-11 show the precision and robustness of the method of the invention. The parameters and conditions described in the example herein are not intended to limit the scope of the invention claimed herein and one skilled in the art will be able without undue experimentation to use the method of the invention as described herein.

I claim:

1. A method for the quantification of perchlorate in a sample comprising the steps of;
   v. providing an extract of a sample, said extract containing the perchlorate to be quantified,
   vi. applying the extract to a reversed phase stationary phase support,
   vii. eluting the extract with a mobile phase comprising an organic solvent, water and organic acid, and
   viii. detecting the eluted perchlorate.

2. The method of claim 1, in which the stationary reverse phase support comprises an alkylated base material, said base material being selected from the group consisting of silica, alumina, zirconia, polystyrene, polyacrylamide, and styrene-divinyl copolymers.

3. The method of claim 2 in which the stationary support further comprises a protein coating.

4. The method of claim 2, in which the surface of said alkylated base material is alkylated with hydrocarbon chains containing from 4-18 carbon atoms.

5. The method of claim 1, in which the organic solvent is selected from the group consisting of methanol, ethanol, acetonitrile, ethyl acetate, and 2-propanol.

6. The method of claim 1 in which the mobile phase has a composition of between 5% and 95% by volume of organic solvent, 5% and 95% by volume of water and 0.05% and 5% by volume of organic acid.

7. The method of claim 1, in which the perchlorate is detected by mass spectrometry.

8. The method of claim 7, in which the perchlorate is detected at a mass of 83 and 85.

9. The method of claim 1 further comprising the step of adding an internal standard to the extract.

10. The method of claim 9 in which the internal standard comprises perchlorate in which O16 is partially replaced by heavy Oxygen (O18).

11. The method of claim 9, where said internal standard is detected at a mass of 89 or 91 or both 89 and 91 together.

12. The method of claim 10, where isotopic mass ratios of chlorine 35 to chlorine 37 in the perchlorate standard comprising O18 are used for confirmation.

* * * * *